(12) United States Patent
Bayborodov

(10) Patent No.: US 10,918,520 B2
(45) Date of Patent: Feb. 16, 2021

(54) METHOD FOR TREATING STAGE 1 MACULAR HOLE WITHOUT VITRECTOMY AND THE INSTRUMENT FOR REALISATION THEREOF

(71) Applicant: Yaroslav Vladimirovich Bayborodov, Lomonosovsky (RU)

(72) Inventor: Yaroslav Vladimirovich Bayborodov, Lomonosovsky (RU)

( * ) Notice: Subject to any disclaimer, the term of this patent is extended or adjusted under 35 U.S.C. 154(b) by 484 days.

(21) Appl. No.: 15/559,844

(22) PCT Filed: Mar. 21, 2016

(86) PCT No.: PCT/RU2016/000152
§ 371 (c)(1),
(2) Date: Sep. 20, 2017

(87) PCT Pub. No.: WO2016/159832
PCT Pub. Date: Oct. 6, 2016

(65) Prior Publication Data
US 2018/0042769 A1  Feb. 15, 2018

(30) Foreign Application Priority Data
Mar. 27, 2015  (RU) .................................. 2015111183

(51) Int. Cl.
*A61F 9/007* (2006.01)

(52) U.S. Cl.
CPC .......... *A61F 9/00736* (2013.01); *A61F 9/007* (2013.01)

(58) Field of Classification Search
CPC .............................. A61F 9/00736; A61F 9/007
See application file for complete search history.

(56) References Cited

U.S. PATENT DOCUMENTS

| 5,597,381 | A | * | 1/1997 | Rizzo, III | ................. A61F 2/14 128/898 |
|---|---|---|---|---|---|
| 8,425,596 | B2 | | 4/2013 | Britton et al. | |

(Continued)

FOREIGN PATENT DOCUMENTS

| RU | 16252 U1 | 12/2000 |
|---|---|---|
| RU | 82117 | 4/2009 |

*Primary Examiner* — Elizabeth Houston
*Assistant Examiner* — Michael G Mendoza
(74) *Attorney, Agent, or Firm* — Gugliotta & Gugliotta, LPA

(57) ABSTRACT

The invention relates to ophthalmology, in particular to the surgical treatment technique of macular holes at the early stages without vitrectomy. The method for treating stage 1 macular hole without vitrectomy comprises peeling the posterior hyaloid membrane away from the foveola, wherein an ophthalmological instrument is inserted through the vitreous body until it comes into contact with the posterior hyaloid membrane in the macular area, the posterior hyaloid membrane then being gripped by said instrument and peeled away from the foveola, in accordance with the invention, and after the contact between the instrument and the posterior hyaloid membrane an opening is made therein, whereby the edge of the opening is then used to lift the posterior hyaloid membrane and peel it away from the foveola until the layers are separated; wherein the instrument used is an ophthalmological membrane spatula comprising a handle 1 and a pointed working part 2 with a tip 3 shaped as a hook. The improved grip of the posterior hyaloid membrane, better visual control and maintaining the hold of said membrane continuously through the manipulations until the peeling from the foveola is complete, made it possible to reduce the trauma associated with surgical management of stage 1 macular hole without vitrectomy and to decrease the number of related complications.

1 Claim, 1 Drawing Sheet

(56) References Cited

U.S. PATENT DOCUMENTS

2009/0240271 A1 9/2009 Britton et al.
2011/0015669 A1* 1/2011 Corcosteugi ............ A61B 17/29
 606/207

* cited by examiner

METHOD FOR TREATING STAGE 1 MACULAR HOLE WITHOUT VITRECTOMY AND THE INSTRUMENT FOR REALISATION THEREOF

TECHNICAL FIELD

The invention relates to ophthalmology, in particular to the surgical treatment technique of macular holes at the early stages without vitrectomy.

BACKGROUND ART

A method for treatment of the first stage of macular holes by intravitreal administration of enzymes, in particular microplasmin, is known from the prior art (see, for example, Stalmans P et al.) <<Intravitreal injection of microplasmin for treatment of vitreomacular adhesion:
results of a prospective, randomized, sham-controlled phase II trial (the MIVI-IIT trial)>>, Retina, 2010 July-August; 30(7): 1122-7, http://www.ncbi.nlm.nih.gov/pubmed/?term=Stalmans+P.2C+Delaey=C.

When the enzyme enters the vitreous body, the collagen protein dissolves, providing the strength of vitreophoveolar adhesion.

The disadvantage of this method is the need to repeat the operation for a number of times. The efficiency of the process as a whole does not exceed 50%. In addition, the drugs used in the implementation of the method have a very high cost.

A method for treatment of the first stage of macular holes is known, including vitrectomy with separation of the posterior hyaloid membrane (PHF) from the foveola, see de Bustros S. "Vitrectomy for prevention of macular holes. Results of a randomized multicenter clinical trial. Vitrectomy for Prevention of Macular Hole Study Group>>, Ophthalmology. 1994 June; 101(6): 1055-9, http://www.ncbi.nlm.nih.gov/pubmed18008347.

Its disadvantage, as well as in the case of other well-known methods envisaging vitrectomy, is the fact that in the course of vitrectomy up to 80% of the vitreous body is removed. At that in more than 80% of cases, cataracts develop intensively (in the next six months), the risks of retinal detachment, glaucoma and loss of visual fields are significantly increased.

The method for treating stage 1macular hole without vitrectomy comprises peeling the posterior hyaloid membrane away from the foveola, wherein an ophthalmological instrument is inserted through the vitreous body until it comes into contact with the posterior hyaloid membrane in the macular area, the posterior hyaloid membrane then being gripped by said instrument and peeled away from the foveola; for an ophthalmological instrument tweezers are used (see L. I. Balashevich, Ya. V. Baybarodov. Sparing surgery of vitreomacular interface pathology without vitrectomy, Ophthalmosurgery, 2011, No. 3, p. 43.

When using this method, the vitreous body is not removed, due to which the technical result is achieved, which consists in reducing the traumatism of treatment and reducing the associated complications, in particular, reducing the risk of cataract development, retinal detachment, glaucoma, loss of vision fields. Instruments are inserted in the vitreous body once, which significantly reduces the risk of infection.

This method is adopted as a prototype of the present invention in a part of the method.

The drawback of the prototype method is the unreliable separation of the posterior hyaloid membrane from the foveola, due to the following circumstances: the tweezers do not allow the delicate entry into the retrohyaloid space; due to the fact that the rods of the tweezers slide off the posterior hyaloid membrane, the tweezers do not allow for its secure grip, as a result of which the separation of the posterior hyaloid membrane from the foveola is not always possible. In addition, the described method does not allow for visual control over the operation, since tweezers overlap the foveola area, making it difficult to visualize the separation of the posterior hyaloid membrane, which leads to uncontrolled ruptures of the wall of the phaeolar cyst.

A device for separating the posterior hyaloid membrane from the retina surface is known from prior art, which is an ophthalmic membrane spatula containing a handle and a pointed working part, RU 82117 U1, publ. Apr. 20, 2009.

With the aid of this device, adopted as a prototype of the present invention in a part of the device, separation of the posterior hyaloid membrane from the foveola is extremely difficult.

SUMMARY OF THE INVENTION

The improved grip of the posterior hyaloid membrane, the better visual control and maintaining the hold or the said membrane continuously through the manipulations until the peeling from the foveola is complete, makes it possible to reduce the trauma associated with surgical management of stage 1 macular hole without vitrectomy and to decrease the number of related complications, which is the object of the invention. Another objective of the invention is to provide a tool that ensures a non-traumatic insertion through the vitreous body before contact with the macula, a reliable grip of the posterior hyaloid membrane and its retention.

According to the invention, in a part of the method, and particularly—in the method for treating stage 1 macular hole without vitrectomy comprises peeling the posterior hyaloid membrane away from the foveola, wherein an ophthalmological instrument is inserted through the vitreous body until it comes into contact with the posterior hyaloid membrane in the macular area, the posterior hyaloid membrane then being gripped by said instrument and peeled away from the foveola, and after the contact between the instrument and the posterior hyaloid membrane an opening is made therein, whereby the edge of the opening is then used to lift the posterior hyaloid membrane and peel it away from the foveola until the layers are separated; wherein the instrument used is an ophthalmological membrane spatula comprising a handle and a pointed working part with a tip shaped as a hook.

According to the invention the tip of the pointed working part of the tool for implementing the method, which is an ophthalmic membrane spatula comprising a handle and a pointed working part, is shaped as a hook.

The Applicant has not found any technical solutions identical to the subject method and the device, which makes it possible to conclude that the inventions comply with the patentability criterion "Novelty" ("N").

The applicant has not found any sources of information containing data on the effect of the distinctive features of the invention on the technical result achieved due to their implementation.

The abovementioned circumstances enable to conclude that the method and the instrument for its implementation conform to the criterion "Inventive Step" (IS).

BRIEF DESCRIPTION OF THE DRAWINGS

In the following, the invention will be explained with a detailed description of examples of its implementation; in the design part—with reference to the drawings, which specify the following.

PREFERRED EMBODIMENT

Figure 1:
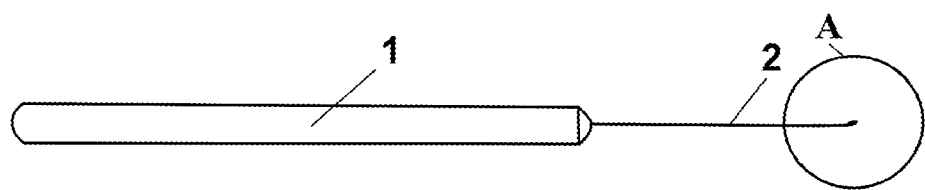
FIG. 1 shows a general view of the device.
Figure 2:
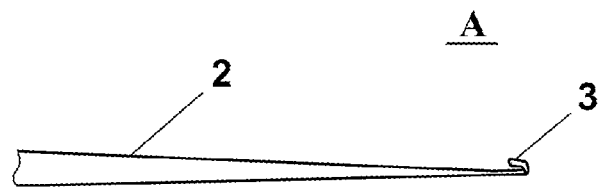
FIG. 2 shows fragment A from FIG. 1 on an enlarged scale.

The instillment used for implementation of the subject method is an ophthalmological membrane spatula comprising a handle 1 and a pointed working part 2 with a tip 3 shaped as a hook. The semantic meaning of the term "membrane spatula" used by the applicant is "a narrow elongated thin elastic plate".

The implementation of the subject method by means of the said tool is explained as follows.

In a patient with the diagnosis of "the first stage 1 of macular hole", two valve ports, which are metal bushings by the diameter of 0.54 mm, are positioned in the vitreal cavity 3-4 mm from the limb on the arc marks of "10 o'clock" and "2 o'clock". The bushings have check valves that pass the instruments into the vitreal cavity and block the flow of fluid from the vitreous body. A light guide with a mercury light source is introduced into one of the ports, providing illumination within 1000-2000 lux. Into the other port, a ophthalmic membrane spatula comprising a handle and a pointed working part with a tip shaped as a hook is inserted through the vitreous body up to contact with the PHF in the macula area. Then, an opening in the PHF is made with the inserted tool, and then using the hook-shaped tip 3 of the working part 2 of the spatula the PHF is lifted and slowly separated from the foveol up to its detachment. Due to the implementation of the tool in the form of a narrow thin plate (membrane spatula), the inserted instrument does not overlap the foveola area, which allows separation of the posterior hyaloid membrane under a clear visual control. After that, the instruments are removed, the openings in the sclera are sealed and the conjunctiva is sutured in the projection of sclerotomy. The total operation duration is, on average, 7-15 minutes.

Owing to the implementation of the distinctive features of the subject invention, the technical result is achieved, which consists in reducing the traumatism of treatment and reducing the associated complications, by increasing the reliability of capture of the posterior hyaloid membrane and its retention in the process of manipulation up to complete separation from the feveola. In addition, the traumatism of treatment is also reduced due to the fact that the separation of the posterior hyaloid membrane is performed under a clear visual control, which allows to eliminate uncontrolled ruptures of the wall of the phoeolar cyst. The vitreous body is not removed, which reduces the risk of cataract development, retinal detachment, glaucoma, loss of vision fields. Instruments are inserted in the vitreous body once, which significantly reduces the risk of infection.

The subject instrument made in the form of a narrow thin plate with a pointed working part ensures a nontraumatic insertion through the vitreous body up to contact with the macula. Thanks to the hook-shaped tip of the working part of the instrument, a reliable grip of the posterior hyaloid membrane is ensured, as well as its retention during manipulation up to complete separation (exfoliation) from the foveola under clear visual control, which allows to increase the efficiency of surgical treatment up to 98%.

INDUSTRIAL APPLICABILITY

The subject invention has been successfully tested in the interbranch scientific and technical complex FSBI "Eye Microsurgery" named after Academician S. N. Fedorov (the St. Petersburg branch), which makes it possible to conclude that the invention complies with the patentability criterion "Industrial Applicability" ("IA").

The invention claimed is:

1. The method for treating stage 1 macular hole without vitrectomy comprising peeling the posterior hyaloid membrane away from the foveola, wherein an ophthalmological instrument is inserted through the vitreous body until it comes into contact with the posterior hyaloid membrane in the macular area, the posterior hyaloid membrane then being gripped by said instrument and peeled away from the foveola,characterized in that after the contact between the instrument and the posterior hyaloid membrane an opening is made therein, whereby the edge of the opening is then used to lift the posterior hyaloid membrane and peel it away from the foveola until the posterior hyaloid membrane and the foveolar are separated; wherein the instrument used is an ophthalmological membrane spatula comprising a handle and a pointed working part with a tip shaped as a hook.

* * * * *